(12) United States Patent
De Lacharriere

(10) Patent No.: US 6,262,050 B1
(45) Date of Patent: Jul. 17, 2001

(54) TOPICAL COMPOSITION CONTAINING CAPSAZEPINE

(75) Inventor: Olivier De Lacharriere, Paris (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 09/457,667

(22) Filed: Dec. 9, 1999

Related U.S. Application Data

(63) Continuation of application No. 09/068,237, filed as application No. PCT/FR96/01592 on Oct. 11, 1996, now Pat. No. 6,048,855.

(30) Foreign Application Priority Data

Nov. 6, 1995 (FR) .................................................. 95/13.096

(51) Int. Cl.⁷ ............................ A01N 43/46; A61K 31/55
(52) U.S. Cl. ....................................................... 514/213.01
(58) Field of Search ............................................. 514/213

(56) References Cited

PUBLICATIONS

BR.J. Pharmacol., vol. 107, No. 2, 1992, pp. 329–333, XP000576708, M.N. Perkins "Capsazepine reversal of the antinociceptive action of capsaicin in vivo".

*Primary Examiner*—Dwayne C. Jones
(74) *Attorney, Agent, or Firm*—Burns, Doane, Swecker & Mathis, L.L.P.

(57) ABSTRACT

A topical composition containing capsazepine and particularly suitable for treating neurogenic skin disorders and diseases, especially painful and/or pruriginous diseases, as well as for treating sensitive skin and eyes, in particular, the composition is useful for preventing and/or controlling skin and/or eye irritation, itching, erythema and dysaesthesia and heating of the skin, eyes and mucosa, as well as for reducing the irritancy of an active substance having an irritant side-effect.

9 Claims, No Drawings

TOPICAL COMPOSITION CONTAINING CAPSAZEPINE

This application is a continuation of application Ser. No. 09/068,237, filed Jun. 18, 1998, now U.S. Pat. No. 6,048,85 which in turn is a 371 of PCT/FR96/01592, filed Oct. 11, 1996.

The present invention relates to a cosmetic, dermatological and/or pharmaceutical composition intended in particular for the treatment in man of certain cutaneous disorders and/or skin diseases, in particular painful and/or pruriginous diseases.

Some of these diseases are currently treated by means of local corticoids or of PUVA therapy. Corticoids are very effective in soothing the symptoms of these diseases but, unfortunately, they exhibit side effects which are often highly disadvantageous such as atrophies or infections, in particular mycotic or bacterial infections. PUVA therapy is, for its part, the local irradiation of the diseased skin with UVA radiation, after absorption of a photosensitizing substance. This technique exhibits the serious disadvantages of a photoageing, which can very often result in cancers of the skin. Moreover, this treatment is not ambulatory, obliging the patients commonly to go to a specialist centre throughout the duration of the treatment, which is highly restricting and limits their occupational employment and their leisure activities.

The precise subject of the present invention is a topical composition which makes it possible to effectively treat these cutaneous diseases, while overcoming these disadvantages.

Moreover, it is known that certain skins are more sensitive than others. Now, the symptoms of sensitive skins were, until now, poorly characterized and no one knew exactly the process implicated in the sensitivity of the skin. Some thought that a sensitive skin was a skin which reacted to cosmetic or pharmaceutical products, others that it was a matter of a skin which reacted to a number of external factors, not necessarily related to cosmetic products.

Some tests were tried in attempting to define sensitive skins, for example tests with lactic acid and with DMSO, which are known to be irritant substances: see, for example, the article by K. Lammintausta et al., Dermatoses, 1988, 36, pages 45–49; and the article by T. Agner and J. Serup, Clinical and Experimental Dermatology, 1989, 14, pages 214–217. However, these tests did not make it possible to characterize sensitive skins.

Moreover, sensitive skins were classified as allergic skins.

Due to this ignorance of the characteristics of sensitive skins, it was, until now, very difficult to treat them, and they were treated indirectly, for example by limiting the employment in cosmetic or dermatological compositions of products with an irritant nature, such as surfactants, preservatives or fragrances.

After many clinical tests, the Applicant has been able to determine the symptoms related to sensitive skins. These symptoms are in particular subjective signs which are essentially dysaesthetic sensations. Dysaesthetic sensations is understood to mean more or less painful sensations felt in a cutaneous region, such as smarting, pins and needles, itching or pruritus, burning sensations, warming sensations, discomfort, stabbing pains, and the like.

In addition, the Applicant has been able to show that a sensitive skin was not an allergic skin. In fact, an allergic skin is a skin which reacts to an external agent, known as an allergen, which triggers an allergic reaction. This relates to an immunological process which only takes place in the presence of an allergen and which only affects sensitized subjects. In contrast, the essential characteristic of sensitive skin is, according to the Applicant, a mechanism of response to external factors which can concern any individual, even if individuals said to have sensitive skins react thereto faster than other individuals. This mechanism is not immunological.

The Applicant has now found that sensitive skins could be divided into two major clinical forms: irritable and/or reactive skins and intolerant skins.

An irritable and/or reactive skin is a skin which reacts by a pruritus, that is to say by itching or by smarting, to different factors, such as the environment, the emotions, food, the wind, friction, shaving, soap, surfactants, hard water with a high calcium concentration, temperature variations or wool. In general, these signs are associated with a dry skin, with or without sores, or with a skin which exhibits an erythema.

An intolerant skin is a skin which reacts with sensations of warming, stabbing pains, pins and needles and/or redness to different factors, such as the environment, the emotions or food. In general, these signs are associated with a hyperseborrhoeic or acneic skin, with or without sores, and with an erythema.

"Sensitive" scalps have a less ambiguous clinical symptomatology: the sensations of pruritus and/or of smarting and/or of warming are essentially trigggered by local factors such as friction, soap, surfactants, hard water with a high calcium concentration, shampoos or lotions. These sensations are also sometimes triggered by factors such as the environment, the emotions and/or food. An erythema and a hyperseborrhoea of the scalp and a dandruff state are frequently associated with the above signs.

Moreover, in certain anatomical regions, such as the major folds (inguinal, genital, axillary, popliteal, anal, submammary or bend of the elbow regions) and the feet, sensitive skin is reflected by pruriginous sensations and/or dysaesthetic sensations (warming or smarting) related in particular to sweat, to friction, to wool, to surfactants, to hard water with a high calcium concentration and/or to temperature variations.

In order to determine if a skin is sensitive or not, the Applicant has also developed a test. In fact, he has found, surprisingly, that there existed a connection between people with sensitive skins and those who reacted to a topical application of capsaicin.

This test with capsaicin consists in applying, to approximately 4 $cm^2$ of skin, 0.05 ml of a cream containing 0.075% of capsaicin and in noting the appearance of subjective signs caused by this application, such a smarting, burning sensations and itching. In subjects with sensitive skins, these signs appear between 3 and 20 minutes after application and are followed by the appearance of an erythema which begins at the periphery of the application region.

Capsaicin causes release of neuropeptides and in particular of tachykinins which arise from nerve endings in the epidermis and in the dermis. The dysaesthetic manifestations which are caused by the release and/or the synthesis and/or the binding of its neuropeptides are known as "neurogenic".

The Applicant has now discovered that, by acting on the cutaneous and ocular receptors sensitive to capsaicin, it was possible to obtain a preventive and/or curative effect with respect to cutaneous and/or mucosal and/or ophthalmological diseases related to the release and/or synthesis and/or binding of neuropeptides, such as shingles, eczema, sensitive skins and eyes, pruritus and pruriginous diseases, herpes, atopic or contact dermatitides, lichens, prurigos, erythemas, in particular sunburn, insect stings, rosacea, conjunctivitis, uveitides, cutaneous or ocular pain, or irritations.

The Applicant has envisaged the use of capsazepine in the treatment of the symptoms associated with these cutaneous diseases and with sensitive skins or eyes in man. In fact, it has been found, surprisingly, that the incorporation of capsazepine in a composition for topical application made it possible to prevent the irritation, the dysaesthetic sensations, the pruritus and the disorders of the skin mentioned above.

The subject of the present invention is therefore a topical composition containing, in a topically and physiologically acceptable medium, capsazepine and at least one active principle with an irritant side effect.

Another subject of the invention is the use of capsazepine in or for the manufacture of a topical composition containing a cosmetically and/or dermatologically acceptable medium for preventing and/or combating cutaneous pain, in particular of neurogenic origin, and more particularly the pain from shingles and in particular the pain which follows shingles, "phantom" pain after limb amputation, the pain due to burns and generally cutaneous pain due to attack on the skin (insect sting, sunstroke, jellyfish sting, and the like).

Thus, a further subject of the present invention is the use of capsazepine in or for the manufacture of a composition for topical application for preventing and/or combating cutaneous and/or ocular irritations, erythemas, pruritus or warming and/or dysaesthetic sensations of the skin, of the eyes or of the mucous membranes, in particular in man.

Another subject of the invention is the use of capsazepine in or for the manufacture of a composition for topical application for preventing and/or combating the symptoms related to shingles, to eczema, to sensitive skins or eyes, to pruriginous diseases, to pruritus, to herpes, to atopic or contact dermatitides, to lichens, to prurigos, to insect stings, to rosacea, to conjunctivitis or to uveitides, in particular in man.

Another subject of the present invention is the use of capsazepine as anti-irritant agent in or for the manufacture of a topical composition.

The clinical signs of sensitive skin according to the Applicant are essentially subjective: smarting, pins and needles, pruritus, stabbing pains or warming sensations and they are sometimes associated with erythemas. These signs are due to non-specific external factors.

A cosmetically, dermatologically or physiologically acceptable medium is, according to the invention, a medium compatible with the skin, including the scalp, the nails, the mucous membranes, the eyes and the hair. The composition of the invention can therefore be applied over the whole of the face, the neck, the hair and the nails or any other cutaneous region of the body.

Capsazepine is an organic molecule with the following formula:

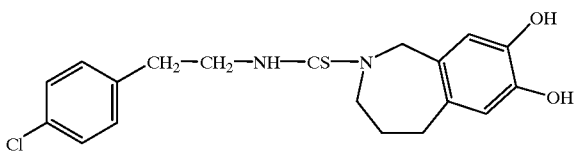

In the compositions according to the invention, capsazepine is preferably used in an amount ranging from 0.000001 to 5% by weight with respect to the total weight of the composition and in particular in an amount ranging from 0.0001 to 0.5% by weight with respect to the total weight of the composition.

The compositions according to the invention can be provided in all the pharmaceutical dosage forms normally used for a topical application, in particular solutions, which may be aqueous, aqueous/alcoholic or oily, or dispersions of the lotion or serum type, emulsions with a liquid or semi-liquid consistency of the mil, type, obtained by dispersion of a fatty phase in an aqueous phase (O/W) or vice versa (W/O), or suspensions or emulsions with a soft consistency of the cream, ointment or aqueous or anhydrous gel type, or alternatively microgranules, or vesicular dispersions of ionic and/or nonionic type. These compositions are prepared according to the usual methods.

These compositions constitute in particular cleansing, protection, treatment or care creams for the face, for the hands, for the feet, for the large anatomical folds or for the body (for example day creams, night creams, make-up removal creams, foundation creams or after-sun creams), liquid foundations, make-up removal products (milks), protective or care body milks, after-sun milks or lotions, lotions, gels or foams for caring for the skin, such as cleansing lotions, artificial tanning lotions, bath compositions, deodorizing compositions comprising a bactericidal agent, after-shave gels or lotions, depilatory creams, compositions for combating insect stings or pain-control compositions.

The compositions according to the invention can also comprise solid preparations consisting of cleansing bars or soaps.

They can also be used for the hair in the form of aqueous, alcoholic or aqueous/alcoholic solutions or in the form of creams, gels, emulsions or foams or alternatively in the form of aerosol compositions also containing a pressurized propellent agent.

The capsazepine can therefore be incorporated in various compositions for hair care and treatment and in particular shampoos, hair-setting lotions, treating lotions, styling creams or gels, dye compositions (in particular oxidation dyes), optionally in the form of colour-enhancing shampoos, hair-restructuring lotions, permanent-wave compositions (in particular compositions for the first step of a permanent wave), lotions or gels for combating hair loss, and the like.

For an application with a therapeutic aim regarding the eyes, the compositions of the invention can be provided in he form of a collyrium, and ointment or an eyewash solution. For a cosmetic application, the compositions can be composed of care or protective creams for sensitive eyes, cleansing or make-up removal milks or lotions for sensitive eyes or make-up products for the eyes, such as crayons, mascaras, eyeliners or eyeshadows.

The cosmetic compositions of the invention can also be for oral use, for example a toothpaste. In this case, the compositions can contain adjuvants and additives usual for compositions for buccal use and in particular surface-active agents, thickening agents, moisturizing agents, polishing agents such as silica, various active ingredients such as fluorides, in particular sodium fluoride, and optionally sweetening agents, such as sodium saccharinate.

The amounts of the different constituents of the compositions according to the invention are those conventionally used in the fields under consideration.

When the composition of the invention is an emulsion, the proportion of the fatty phase can range from 5% to 80% by weight, and preferably from 5% to 50% by weight, with respect to the total weight of the composition. The oils, the emulsifiers and the coemulsifiers used in the composition in the emulsion form are chosen from those conventionally used in the cosmetics field. The emulsifier and the coemulsifier are present, in the composition, in a proportion ranging from 0.3% to 30% by weight, and preferably from 0.5 to 30% by weight, with respect to the total weight of the composition. The emulsion can, in addition, contain lipid vesicles.

In a known way, the composition of the invention can also contain adjuvants which are usual in the field under consideration, such as hydrophilic or lipophilic gelling agents, hydrophilic or lipophilic additives, preservatives, antioxidants, solvents, fragrances, fillers, screening agents and colouring materials, odour absorbers or pigments. The amounts of these different adjuvants are those conventionally used in the field under consideration and, for example, from 0.01% to 20% of the total weight of the composition. These adjuvants, depending on their nature, can be introduced in the fatty phase, in the aqueous phase and/or in the lipid spherules.

Mention may be made, as oils which can be used in the invention, of mineral oils (liquid petrolatum), vegetable oils (liquid fraction of karite butter, sunflower oil), animal oils (perhydrosqualene), synthetic oils (purcellin oil), silicone oils (cyclomethicone) and fluorinated oils (perfluoropolyethers. Fatty alcohols and fatty acids (stearic acid), as well as waxes (paraffin wax, carnauba wax or beeswax, can be added to these oils.

Mention may be made, as emulsifiers which can be used in the invention, of, for example, glyceryl stearate, polysorbate 60 and the PEG-6/PEG-32/glycol stearate mixture sold under the name of Tefose®63 by the company Gattefosse.

Mention may be made, as solvents which can be used in the invention, of lower alcohols, in particular ethanol and isopropanol.

Mention may be made, as hydrophilic gelling agents, or carboxyvinyl polymers (carbomer), acrylic copolymers such as acrylate/alkyl acrylate copolymers, polyacrylamides, polysaccharides such as hydroxypropylcellulose, natural gums and clays and mention may be made, as lipophilic gelling agents, of modified clays such as bentones, metal salts of fatty acids such as aluminium stearates, hydrophobic silica, polyethylenes and ethylcellulose.

Use may be made, as hydrophilic active principles, of proteins or protein hydrolysates, amino acids, polyols, urea, allantoin, sugars and sugar derivatives, hydrophilic vitamins and plant and bacterial extracts.

Use may be made, a lipophilic active principles, of retinol (vitamin A) and its derivatives, tocopherol (vitamin E) and its derivatives, essential fatty acids, ceramides or essential oils.

It is possible, inter alia, to combine capsazepine with active agents intended in particular for the prevention and/or the treatment of the above cutaneous conditions.

Mention may be made, among these active agents, or, by way of example:

agents which modulate cutaneous pigmentation and/or proliferation and/or differentiation, such as retinoic acid and its isomers, retinol and its esters, vitamin D and its derivatives, oestrogens, such as oestradiol, kojic acid or hydroquinone;

antibacterials, such as clindamycin phosphate, erythromycin or antibiotics from the tetracycline class;

agents for combating parasites, in particular metronidazole, crotamiton or pyrethroids;

antifungals, in particular compounds belonging to the imidazole class, such as econazole, ketoconazole or miconazole or their salts, polyene compounds, such as amphotericin B, compounds of the allylamine family, such as terbinafine, or alternatively octopirox;

steroidal anti-inflammatory agents, such as hydrocortisone, betamethasone valerate or clobetasol propionate, or non-steroidal anti-inflammatory agents, such as ibuprofen and its salts, diclofenac and its salts, acetylsalicylic acid, acetaminophen or glycyrrhetinic acid;

anaesthetic agents, such as lidocaine hydrochloride and its derivatives;

antipruriginous agents, such as thenaldine, trimeprazine or cyproheptadine;

antiviral agents, such as acyclovir;

keratolytic agents, such as α- and β-hydroxycarboxylic acids or β-ketocarboxylic acids, theirs salts, amides or esters and more particularly hydroxy acids, such as glycolic acid, lactic acid, salicylic acid, citric acid and generally fruit acids, and 5-(n-octanoyl)salicylic acid;

agents for combating free radicals, such as α-tocopherol or its esters, superoxide dismutases, certain metal chelating agents or ascorbic acid and its esters;

antiseborrhoeics, such as progesterone;

antidandruff agents, such as octopirox or zinc pyrithione;

antiacne agents, such as retinoic acid or benzoyl peroxide.

According to the invention, capsazepine is combined with active principles with an irritant side effect commonly used in the cosmetic or dermatological fields. The presence of capsazepine in a composition containing an active principle having an irritant effect makes it possible to greatly reduce or indeed eliminate this irritant effect.

In particular, the active principles with an irritant side effect are chosen from α-hydroxy acids, β-hydroxy acids, α-keto acids, β-keto acids, retinoids, anthralins, anthranoids, peroxides, minoxidil, lithium salts, antimetabolites, vitamin D and its derivatives, aluminium salts, surfactants, reducing agents, oxidizin agents, strong bases (ammonia or monoethanolamine) or strong acids.

An additional subject of the present invention is a cosmetic or dermatological treatment process, characterized in that a composition as described above containing capsazepine in a cosmetically acceptable medium is applied on the skin, the eyes, the hair and/or the mucous membranes.

The treatment process of the invention can be implemented in particular by applying the hygiene or cosmetic compositions as defined above according to the usual technique for the use of these compositions. For example: application of after-sun compositions or make-up removal milks, lotions, serums, gels or creams on the skin or on dry hair, application of a hair lotion on wet hair or of shampoos, or alternatively application of a dentifrice on the gums.

The following examples illustrate the invention. In these examples, the proportions shown are percentages by weight.

EXAMPLE 1

Make-up removal lotion for the face

| | | |
|---|---|---|
| Capsazepine | | 0.03 |
| Antioxidant | | 0.05 |
| Isopropanol | | 40.00 |
| Preservative | | 0.30 |
| Water | q.s. for | 100% |

EXAMPLE 2

Facial care cream (oil-in-water emulsion)

| | |
|---|---|
| Capsazepine | 0.02 |
| Glyceryl stearate | 2.00 |

-continued

| | | |
|---|---|---|
| Polysorbate 60 (Tween 60, sold by the Company ICI) | | 1.00 |
| Stearic acid | | 1.40 |
| Triethanolamine | | 0.70 |
| Carbomer | | 0.40 |
| Liquid fraction from karite butter | | 12.00 |
| Perhydrosqualene | | 12.00 |
| Antioxidant | | 0.05 |
| Fragrance | | 0.5 |
| Preservative | | 0.30 |
| Water | q.s. for | 100% |

EXAMPLE 3

Shampoo

| | | |
|---|---|---|
| Sodium magnesium lauryl ether sulphate containing 4 mol of ethylene oxide, sold under the name of Texapon ASV by Henkel (anionic surfactant) | | 6.50 |
| Capsazepine | | 0.02 |
| Hydroxypropylcellulose (Klucel H, sold by the Company Hercules) | | 1.00 |
| Fragrance | | 0.50 |
| Preservative | | 0.30 |
| Water | q.s. for | 100% |

EXAMPLE 4

Anti-wrinkle care cream for the face (oil-in-water emulsion)

| | | |
|---|---|---|
| Capsazepine | | 0.03 |
| Glyceryl stearate | | 2.00 |
| Polysorbate 60 (Tween 60, sold by the Company ICI) | | 1.00 |
| Stearic acid | | 1.40 |
| 5-(n-Octanoyl)salicylic acid | | 0.50 |
| Triethanolamine | | 0.70 |
| Carbomer | | 0.40 |
| Liquid fraction from karite butter | | 12.00 |
| Perhydrosqualene | | 12.00 |
| Antioxidant | | 0.05 |
| Fragrance | | 0.5 |
| Preservative | | 0.30 |
| Water | q.s. for | 100% |

EXAMPLE 5

Emulsified gel for the care of insect stings (oil-in-water emulsion)

| | | |
|---|---|---|
| Cyclomethicone | | 3.00 |
| Purcellin oil (sold by the Company Dragocco) | | 7.00 |
| PEG-6/PEG-32/Glycol stearate (Tefose ® 63 from Gattefosse) | | 0.30 |
| Capsazepine | | |
| Preservative | | 0.15 |
| Fragrance | | 0.40 |
| Carbomer | | 0.60 |
| Crotamiton | | 5.00 |
| Glycyrrhetinic acid | | 2.00 |
| Ethyl alcohol | | 5.00 |
| Triethanolamine | | 0.20 |
| Water | q.s. for | 100% |

EXAMPLE 6

Pain-control gel, in particular for the pain associated with shingles

| | | |
|---|---|---|
| Capsazepine | | 0.30 |
| Hydroxypropylcellulose (Klucel H, sold by the Company Hercules) | | 1.00 |
| Antioxidant | | 0.05 |
| Lidocaine hydrochloride | | 2.00 |
| Isopropanol | | 40.00 |
| Preservative | | 0.30 |
| Water | q.s. for | 100% |

EXAMPLE 7

Face cream for the care of rosacea (oil-in-water emulsion)

| | | |
|---|---|---|
| Capsazepine | | 0.25 |
| Glyceryl stearate | | 2.00 |
| Polysorbate 60 (Tween 60, sold by the Company ICI) | | 1.00 |
| Stearic acid | | 1.40 |
| Metronidazole | | 1.00 |
| Triethanolamine | | 0.70 |
| Carbomer | | 0.40 |
| Liquid fraction from karite butter | | 12.00 |
| Liquid petrolatum | | 12.00 |
| Antioxidant | | 0.05 |
| Fragrance | | 0.5 |
| Preservative | | 0.30 |
| Water | q.s. for | 100% |

EXAMPLE 8

Cream for caring for sensitive skins with respect to sunburn (oil-in-water emulsion) or for treating the symptoms relating to shingles

| | | |
|---|---|---|
| Capsazepine | | 0.25 |
| Glyceryl stearate | | 2.00 |
| Polysorbate 60 (Tween 60, sold by the Company ICI) | | 1.00 |
| Stearic acid | | 1.40 |
| Glycyrrhetinic acid | | 2.00 |
| Triethanolamine | | 0.70 |
| Carbomer | | 0.40 |
| Liquid fraction from karite butter | | 12.00 |
| Sunflower oil | | 10.00 |
| Antioxidant | | 0.05 |
| Fragrance | | 0.5 |
| Preservative | | 0.30 |
| Water | q.s. for | 100% |

EXAMPLE 9

Ocular collyrium

| | | |
|---|---|---|
| Capsazepine | | 0.03 |
| Excipient | q.s. for | 100 |
| Sodium chloride | | |
| Sodium borate | | |
| Polysorbate 80 | | |
| Boric acid | | |
| Water | | |

What is claimed is:

1. A method for treating cutaneous pain, said method comprising topically applying an effective amount of capsazepine to a patient in need of such treatment to prevent and/or combat cutaneous pain.

2. A method for treating cutaneous and/or ocular irritation, erythemas, pruritus or warming and/or dysaesthetic sensations of the skin, the eyes or mucous membranes, said method comprising topically applying an effective amount of capsazepine to a patient in need of such treatment to prevent and/or combat cutaneous and/or ocular irritation, erythema, pruritus or warming and/or dysaesthetic sensations of the skin or the eyes.

3. A method for treating symptoms related to shingles, eczema, sensitive skin or eyes, pruriginous diseases, pruritus, herpes, atopic or contact dermatitides, lichens, prurigos, insect stings, rosacea, conjunctivitis or uveitides, said method comprising topically applying an effective amount of capsazepine to a patient in need of such treatment to prevent and/or combat symptoms related to shingles, eczema, sensitive skin or eyes, pruriginous diseases, pruritus, herpes, atopic or contact dermatitides, lichens, prurigos, insect stings, rosacea, conjunctivitis or uveitides.

4. The method according to claim 1, wherein capsazepine is used in an amount ranging from 0.000001 to 5% by weight with respect to the total weight of the composition.

5. The method according to claim 2, wherein capsazepine is used in an amount ranging from 0.000001 to 5% by weight with respect to the total weight of the composition.

6. The method according to claim 3, wherein capsazepine is used in an amount ranging from 0.000001 to 5% by weight with respect to the total weight of the composition.

7. The method according to claim 4, wherein capsazepine is used in an amount ranging from 0.00001 to 0.5% by weight with respect to the total weight of the composition.

8. The method according to claim 5, wherein capsazepine is used in an amount ranging from 0.00001 to 0.5% by weight with respect to the total weight of the composition.

9. The method according to claim 6, wherein capsazepine is used in an amount ranging from 0.00001 to 0.5% by weight with respect to the total weight of the composition.

* * * * *